(12) United States Patent
Baumann et al.

(10) Patent No.: US 11,167,136 B2
(45) Date of Patent: Nov. 9, 2021

(54) DEVICE AND METHOD FOR ELECTRIC STIMULATION WITH THE AID OF A COCHLEA-IMPLANT

(71) Applicant: MED-EL Elektromedizinische Geraete GmbH, Innsbruck (AT)

(72) Inventors: Uwe Baumann, Frankfurt am Main (DE); Tobias Rader, Mainz (DE)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 367 days.

(21) Appl. No.: 15/561,549

(22) PCT Filed: Mar. 24, 2016

(86) PCT No.: PCT/EP2016/056636
§ 371 (c)(1),
(2) Date: Dec. 14, 2017

(87) PCT Pub. No.: WO2016/151106
PCT Pub. Date: Sep. 29, 2016

(65) Prior Publication Data
US 2018/0161578 A1    Jun. 14, 2018

(30) Foreign Application Priority Data

Mar. 26, 2015   (DE) .......................... 102015104614.8

(51) Int. Cl.
*A61N 1/36* (2006.01)
*A61N 1/05* (2006.01)
(Continued)

(52) U.S. Cl.
CPC ......... *A61N 1/36038* (2017.08); *A61N 1/025* (2013.01); *A61N 1/0541* (2013.01);
(Continued)

(58) Field of Classification Search
CPC ................ A61N 1/36038; A61N 1/025; A61N 1/36036; A61N 1/0541
(Continued)

(56) References Cited

U.S. PATENT DOCUMENTS 5,601,617 A    2/1997 Loeb et al.
7,010,354 B1 *  3/2006 Grayden ............ A61N 1/36038
                                                            607/57
(Continued)

FOREIGN PATENT DOCUMENTS

EP    0 823 188 A1    2/1998
EP    1 210 847 A1    6/2002
WO    WO 2013/152077 A1    10/2013

OTHER PUBLICATIONS

European Patent Office, International Search Report—Application No. PCT/EP2016/056636, dated Oct. 13, 2016, 17 pages (In German).

(Continued)

*Primary Examiner* — Amanda K Hulbert
*Assistant Examiner* — Philip C Edwards
(74) *Attorney, Agent, or Firm* — Sunstein LLP

(57) ABSTRACT

The invention relates to a device (10) and to a method for electric stimulation. Said device comprises a stimulator (12) which comprises a multi-channel electrode arrangement with several stimulation electrodes (E1-E12). Said device also comprises a processor (18) which determines the pulse rate and the pulse amplitude for each stimulation electrode (E1-E12), and which controls the electrode arrangement for releasing stimulation impulses of the determined pulse rate and pulse amplitude. Said processor (18) determines the pulse rate for each stimulation electrode (E1-E12) dependent on the position in the cochlea. The invention also relates to a computer program product by means of which a data (Continued)

processing system determines the pulse rate for each stimulation electrode (E1-E12) dependent on the actual position thereof.

18 Claims, 13 Drawing Sheets

(51) Int. Cl.
    *H04R 25/00*     (2006.01)
    *A61N 1/02*     (2006.01)
(52) U.S. Cl.
    CPC ......... *A61N 1/36039* (2017.08); *H04R 25/48* (2013.01); *H04R 25/502* (2013.01); *H04R 25/70* (2013.01)
(58) Field of Classification Search
    USPC .......................................................... 607/57
    See application file for complete search history.

(56) References Cited

U.S. PATENT DOCUMENTS

| | | | |
|---|---|---|---|
| 2005/0203590 A1* | 9/2005 | Zierhofer | H04R 25/505 607/57 |
| 2011/0077712 A1* | 3/2011 | Killian | A61N 1/36038 607/57 |
| 2013/0006328 A1 | 1/2013 | Bouchataoui et al. | |
| 2015/0088225 A1 | 3/2015 | Noble et al. | |

OTHER PUBLICATIONS

European Patent Office, International Search Report—Application No. PCT/EP2016/056636, dated Oct. 13, 2016, 12 pages (English Translation).

* cited by examiner

DEVICE AND METHOD FOR ELECTRIC STIMULATION WITH THE AID OF A COCHLEA-IMPLANT

CROSS-REFERENCE TO RELATED APPLICATIONS

This Application is a U.S. national stage entry under 35 USC §371 of Patent Cooperation Treaty Application PCT/EP2016/056636, filed Mar. 24, 2016, which claims priority from German Patent Application 10 2015 104 614.8, filed Mar. 26, 2015, both of which are incorporated herein by reference in their entireties.

TECHNICAL FIELD

The invention relates to a device and a method for electrical stimulation with a stimulator which comprises a multi-channel electrode arrangement having a plurality of stimulation electrodes. Furthermore, a processor determines the pulse rate and the pulse amplitude for each stimulation electrode and controls the same electrode arrangement for emitting stimulation pulses with the fixed pulse rate and pulse amplitude. The invention further relates to a computer program product for determining the control of each stimulation electrode of a multichannel electrode arrangement.

BACKGROUND ART

Via electrical stimulation of a patient ear supplied with a cochlear implant, depending on the position of the electrode, an individual perception of a particular pitch in the patient can be achieved, as described e.g. within the document by Baumann, U; Nobbe, A. (2006): *The cochlear implant electrode-pitch function*. In: Hear Res 213, p. 34-42. DOI: 10.1016/j.heares.2005.12.010. In a healthy non-hearing impaired patient, the mechanical oscillations coming from the outside are converted into neural pulses in the cochlea in an anatomically ordered manner according to frequency, respectively according to the pitch. High frequencies are detected at the outer end and low frequencies at the inner end of the cochlea. Thus by local resolution, the pitch is determined, which in turn is detected and further processed by the brain.

During listening, the sound waves received from the outside are transmitted to liquid chambers in the cochlea by the movement of the stirrup via the oval window. Due to the wave-like expansion of a displacement of liquid on account of a recorded sound wave, a travelling deflection occurs of the basilar membrane which divides the cochlea into two chambers filled with perilymph and connected at the helicotrema. The cortic organ with hair cells is located on the basilar membrane.

In patients with a cochlear implant, it is desired to generate a sound perception corresponding to the sound information. For this purpose, the sound vibration that contains the sound information is detected with the aid of a microphone, and with the aid of a stimulation strategy by stimulation of corresponding stimulation electrodes of an implanted multichannel electrode array stimulated. Acoustic signals are thus converted by the cochlear implant into electrical stimulation signals.

Deaf or severely hearing-impaired patients who are supplied with a cochlear implant can only in a very limited manner identify pitch information of a stimulated sound signal. For these patients, the ability to distinguish small pitch changes is greatly reduced. Normal hearing persons can in general recognize changes of the frequency below one percent difference. Patients with a cochlear implant require on average more than 20% frequency difference in order to distinguish a difference in pitch. For this reason, the hearing of music and the recognition of prosodic voice information in patients with a cochlear implant are strongly restricted. Known stimulation strategies for controlling the stimulation electrodes of a multi-channel cochlear implant for transmitting an acoustic signal use one of anatomical mean values, or in theoretical and clinical analysis, found distribution of frequency bands of the stimulation electrodes of a multi-channel cochlear implant. Also known in the prior art is to adjust the stimulation rate of the stimulation pulses from up to four apical electrodes located at the tip of an electrode carrier to the signal frequency of the acoustic signal. In this case, phase synchronization of the electrical stimulation with the phase of the acoustic input signal takes place and thus improved mapping of the temporal fine structure of the signal. Test results in patients do not show significant improvement in the perception of pitch differences.

SUMMARY

The invention relates to a device and a method for the electrical stimulation by means of which a mapping of the pitch information of users with cochlea implants is improved. The invention further relates to a computer program product by means of which a suitable pulse rate can be determined for each stimulation electrode of a multichannel electrode arrangement.

The object is achieved by a device having the features of claim 1 and by a method having the features of claim 14, a computer program product having the features of claim 15 and a method for setting pulse rates for controlling stimulation electrodes of a cochlear implant according to claim 16. Such a method for determining pulse rates can form a component of a method for the patient-specific configuration of a cochlear implant. Advantageous refinements are characterized in the dependent claims.

By means of a device for electrical stimulation, in particular by determining the pulse rate for each stimulation electrode, depending on their position in the cochlea, for people using cochlear implants the mapping of the pitch information, that is to say the perception of the pitch information, can be decisively improved so that even relatively small pitch differences can be perceived. In addition, the mapping of prosodic speech information is also improved, which facilitates both speech understanding in the surrounding of interference noises as well as understanding of tonal languages such as, for example, Chinese. The respective electrical stimulation rate is preferably determined for each stimulation electrode as a function of the corresponding insertion angle, which means it is determined by its insertion depth.

The stimulator preferably has 8 to 30, in particular 12 to 25, stimulation electrodes, for example 12, 16, 22 or 25 stimulation electrodes.

It is advantageous that the stimulator is at least part of a cochlear implant.

Furthermore, it is advantageous that the processor controls the stimulation electrodes depending on their position in the cochlea. In this way, desired pitch information can be easily stimulated.

It is further advantageous, if for at least one stimulation electrode with a corresponding assigned pitch, the processor determines, dependent on the amplitude of the to be stimulated sound information, the stimulation pulse amplitude to be delivered by the stimulation electrode. Thereby the volume of sound information to be stimulated can be determined in a simple manner. The determined amplitude of the sound information to be stimulated is in particular dependent on the sound captured by a sensor unit, such as a microphone. Furthermore, each stimulation electrode can have assigned a pitch range or pitch spectrum, wherein preferably the mean value of the amplitudes of the sound information to be stimulated for the pitch in this pitch range serves as the amplitude of the sound information to be stimulated.

The processor can pre-determine the pulse rate on each stimulation electrode in a fixed manner. Alternatively, the processor can determine the pulse rate for the stimulation electrode depending on the pitch of a tone sequence to be stimulated. As a result, the perception of the pitch of a sound information to be stimulated in a person wearing a cochlear implant can be further improved. Furthermore, it is advantageous that the processor, dependent on the pitch of a sound information to be stimulated, selects at least one stimulation electrode for the stimulation of said sound information and controls the stimulation electrode for delivery of stimulation pulses at the pulse rate defined for said stimulation electrode. Thereby, the sound information of a tone having a special pitch can be further improved and/or a plurality of tone information can be stimulated simultaneously.

Furthermore, it is advantageous if the electrode arrangement comprises a plurality of monopolar stimulation electrodes. In this way, known cost-effective electrode arrangements can be used in the device.

Furthermore, it is advantageous that the device has an image-generating unit which determines at least one image of at least one stimulation electrode implanted in a patient body. The image generating unit can determine the image in particular with the aid of a radiographic method, in particular by means of planar x-ray computed tomography, digital volume tomography or magnetic resonance tomography.

It is particularly advantageous that for each stimulation electrode, the expected pitch perception is determined depending on the position in the cochlea. The expected pitch percept can be in particular calculated with a mathematical function.

Furthermore, it is advantageous to determine the position of the stimulation electrode by the insertion angle. Thereby, a simple position determination and indication of the position of each stimulation electrode is possible.

Furthermore, it is advantageous that based on the position determined for each stimulation electrode, a basic tonotopy arrangement is determined. Tonotopy as used herein refers to the first main stage of the sound analysis in the cochlea, in which the mechanical vibrations coming from the outside are converted into neural pulses.

The determined basic tonotopy arrangement for all the stimulation electrodes is also referred to as a basic tonotopy-map. It is particularly advantageous, that the processor individually determines the stimulation rate of each individual stimulation electrode such that the pitch perception indicated in the basic tonotopy arrangement is generated at the respective stimulation position. This enables that the stimulation electrodes can be controlled in a simple manner such that a desired pitch perception can also be generated for pitches for which no stimulation electrode is directly assigned, but rather a plurality of stimulation electrodes for generation of the pitch perception.

In particular, the processor can generate the pitch perception by means of a weighted parallel stimulation of adjacent stimulation electrodes. As a result, in particular the stimulation of a pitch perception of any desired pitch is possible in a relatively simple manner. Additionally or alternatively, the processor can determine the pulse amplitude by means of a weighted parallel stimulation of adjacent stimulation electrodes. Excessively strong local stimulation with only one electrode, in particular at high volume levels, is thereby prevented. This is also energy efficient. In particular, a suitable control of adjacent electrodes with different amplitudes is considered to be a weighted parallel stimulation. Furthermore, the processor can check after determining the pulse rate and/or the pulse amplitude, whether a local superelevation of an electric field generated by the stimulation electrodes generates an excessively loud perception. The processor can then reduce the pulse amplitude and/or the number of pulses in the event of a detected superelevation.

Furthermore, it is advantageous that comparisons of the preset nominal and the actual position of every stimulation electrode are made and the processor determines based on the ascertained deviation of the preset nominal to the actual position for each stimulation electrode a correction factor and based on the correction factor the pulse rate that has to be generated by the electrode, starting with the determined pulse rate of the nominal position.

A second aspect of the invention relates to a method for controlling stimulation electrodes of an electrode arrangement of a stimulator in which the pulse rate and the pulse amplitude for each stimulation electrode are determined, and where the electrode arrangement is controlled to emit the defined pulse amplitude and pulse rate. The actual position of each stimulation electrode is determined and the pulse rate for each stimulation electrode is determined as a function of its determined position in the cochlea. In particular, the electrode arrangement with the stimulation electrodes is implanted in the patient's body. In this way, improved stimulation of the pitch of sound information to be stimulated is possible.

A third aspect relates to a computer program product comprising commands and data in coded form which cause a data processing system, after the program data has been loaded, to determine the pulse rate for each stimulation electrode of a multichannel electrode arrangement depending on its actual position in the cochlea. The data processing system can be a processor of a device for stimulating sound information at a person with an implanted cochlea implant. With the aid of such a computer program product, the stimulation electrodes can be controlled at a pulse rate were an improved stimulation of pitch information is possible.

In all aspects of the invention, in the case of persons with a cochlear implant, a pitch percept corresponding to the normal tonotopy is achieved.

Further features and advantages result from the following description. The invention is explained in more detail by means of exemplary embodiments in connection with the attached figures.

DETAILED DESCRIPTION

Figure 1:
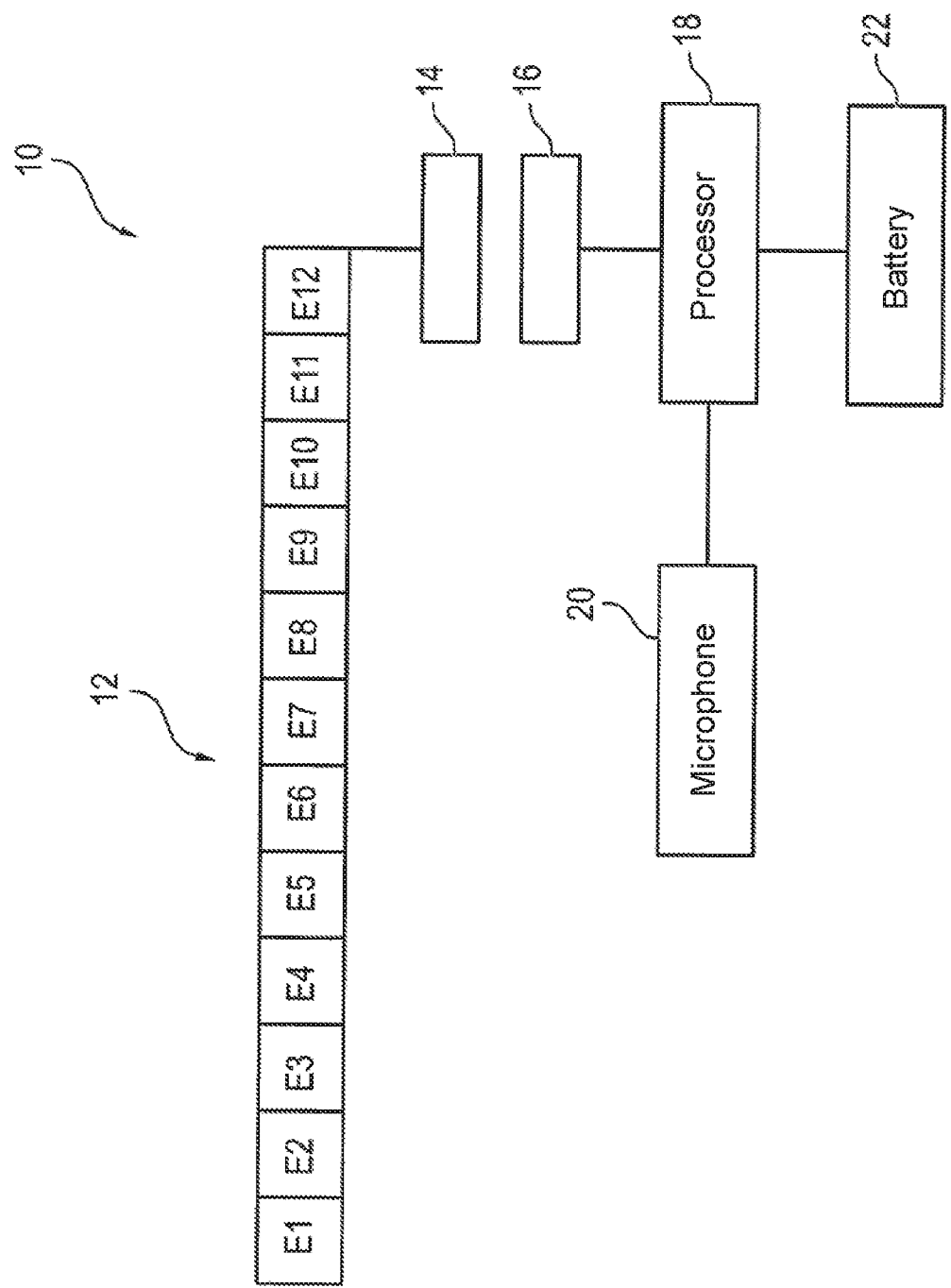
FIG. 1 a block diagram of a device for stimulation.

FIG. 1 shows a schematic block diagram of a device 10 for stimulating the cochlea of a patient in order to generate a sound perception in a hearing-impaired or deaf person. The device has a stimulator 12, which in the present exemplary embodiment has twelve electrodes E1 to E12 as well as one drive circuit for driving the electrodes E1 to E12 for delivering stimulation pulses. The stimulator 12 is coupled to a digital speech processor 18 via a receiving coil 14 and a transmitting coil 16. The transmitting coil 16 and the receiving coil 14 are used for the wireless signal and energy supply between the processor 18 and the stimulator 12. Electrodes E1 to E12 are implanted together with the control circuit of the stimulator 12 into the cochlea of the patient. The stimulator 12 with the electrodes E1 to E12 is also referred to as a cochlear implant. In addition, the receiving coil 14 is implanted in the head of the patient.

The processor 18 is coupled to a microphone 20 and supplied with energy via a battery 22. The microphone 20, the processor 18 and the battery 22 as well as the transmission coil 16 are usually arranged on the outside of the head of the patient. Conventional receiving coils 14 and transmission coils 16 each comprise a magnet by means of which the transmitting coil 16 and the receiving coil 14 are held in a position required for coupling the transmitting coil 16 and the receiving coil 14. The processor processes the sound information recorded with the aid of the microphone 20 and determines both the pulse rate and the pulse amplitude for each stimulation electrode E1 to E12, and controls the electrode arrangement comprising electrodes E1 to E12 of the stimulator 12 in order to deliver corresponding stimulation pulses.

According to the invention, the processor 18 determines the pulse rate of each stimulation electrode E1 to E12 corresponding to its actual position, i.e. depending on its actual position in the cochlea. For this purpose, the actual position of each stimulation electrode is determined exactly after the implantation of the stimulator 12 into the body of the patient. For this purpose, in particular, an image of the cochlea with the implanted electrodes E1 to E12 is recorded, for example, with the aid of a radiographic imaging method such as, for example, planar x-ray, computer tomography, digital volume tomography or magnetic resonance tomography. Based on a recorded image, the position of each electrode E1 to E12 can then be automatically determined with the aid of suitable image processing software or can be determined manually from the recorded image. The position is specified in particular by an insertion angle for each electrode E1 to E12 which indicates the insertion depth of the respective electrode in the cochlea. The image is recorded following the implantation of the electrode arrangement E1 to E12 into the patient. In order to improve the determination of the position of each electrode in the cochlea, a plurality of images can also be recorded and evaluated.

Figure 2:
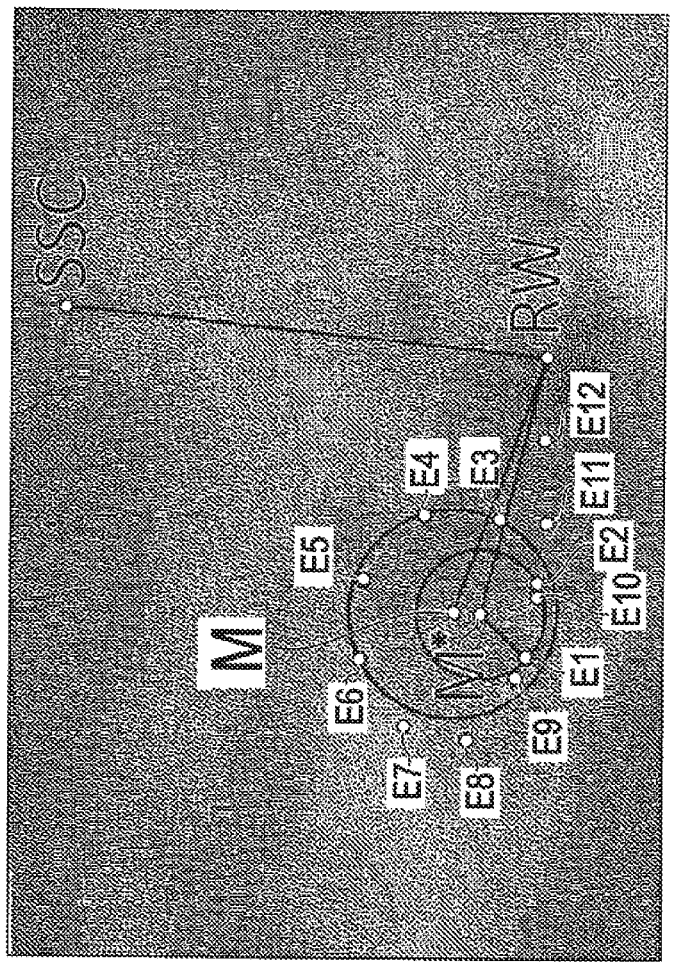
FIG. 2 a simplified x-ray image with the marking of the position of a total of twelve stimulation electrodes of a cochlear implant with additional auxiliary lines drawn for determining the insertion angle of a first stimulation electrode E1.
Figure 3:
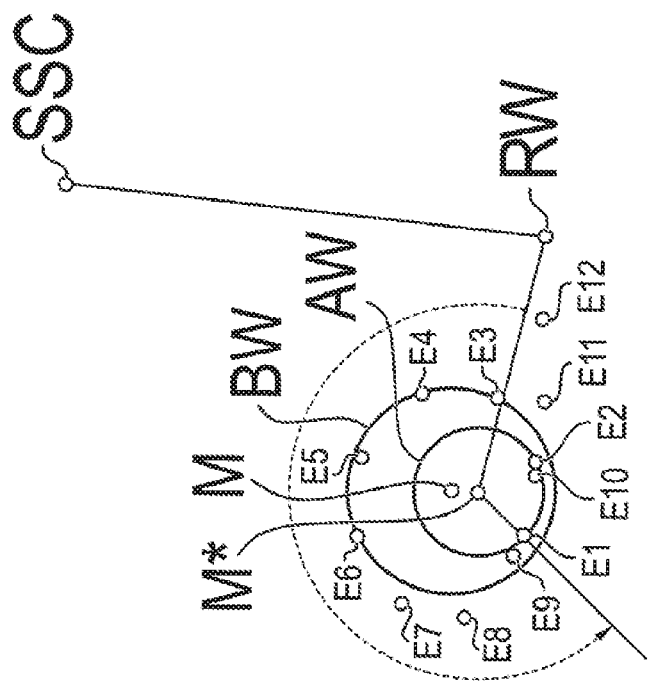
FIG. 3 the schematic drawing of the positions of the stimulation electrodes of the cochlear implant according to FIG. 2 showing further auxiliary lines for determining the insertion angle of the first stimulation electrode E1.

FIG. 2 shows a x-ray image of the cochlea with a total of twelve positions of the electrodes E1 to E12 of the stimulator 12 marked by circles, that has been recorded in a post-operative manner. In particular, the image can also be used as a modified Seenver's view, digital volume tomography of the petrous part of the temporal bone or as a high-resolution computed tomography of the petrous part of the temporal bone using suitable reconstruction methods for the highly accurate estimation of the insertion angle. The zero point of the insertion angle is determined via the point of intersection of an electrode carrier of the electrodes E1 to E12 with the connecting line of the superior arc path SSC to the vestibular, as described in Cohen, L. T.; Xu, J; Xu, S.A.; Clark, G. M. (1996): Improved and simplified methods for specifying positions of the electrode bands of a cochlear implant array. In: Am J Otol 17, pp. 859-65, Online available under http://www.ncbi.nlm.nih.gov/pubmed/8915414; and Xu, J; Xu, S. A.; Cohen, L. T.; Clark, G. M. (2000): Cochlear view: postoperative radiography for cochlear implantation. In: Am J Otol 21, pp. 49-56; Online available under http://www.ncbi.nlm.nih.gov/pubmed/10651435. The zero point serves as a geometric zero reference, as is also the case in Boex, C.; Baud, L.; Cosendai, G.; Sigrist, A.; Kos, M. I.; Pelizzone, M. (2006): Acoustic to electric pitch comparison in cochlear implant subjects with residual hearing. In: Journal of the association for research in Otolaryngology: JARO 7, p. 110-24 DOI: 11007/s10162-005-0027-2. This intersection point corresponds to the round window RW of the cochlea and defines, upon insertion of the stimulator into the round window RW, the 0-degree reference line for the Electrodes E1 to E6 arranged in the apical winding AW. The center point M* of the apical turn AW is defined as the center of rotation of the insertion angle. For the basal winding BW of the cochlea, the center point M* is placed in the center of the basal electrodes E7 to E12. The connection between the center point M* and the intersection point defines a so-called 720-degree line, as is also the case in Verbist; B. M.; Skinner, Margaret W.; Cohen, L. T.; Leake, P. A.; James, C.; Boex, C. et al (2010): Consensus panel on a cochlear coordinate system applicatable in histologic, physiologic, and radiologic studies of the human cochlea. In: Otol Neurotol 31, pp. 722-30 DOI: 10.1097/MAO.0b013e3181d279e0 and Boex, C.; Baud, L.; Cosendai, G.; Sigrist, A.; Kos, M. I.; Pelizzone, M. (2006): Acoustic to electric pitch comparisons in cochlear implant subjects with residual hearing. In: Journal of the Association for Research in Otolaryngology: JARO 7, pp. 110-24 DOI: 11007/s10162-005-0027-2. The position identified by SSC indicates the superior curved path. As can be seen from FIG. 3, the insertion angle of the electrode E1 in this specific embodiment is 461.2 degrees.

In the exemplary embodiment shown, the electrodes E1 to E6 are arranged in the apical winding AW and the electrodes E7 to E12 are arranged in the basal winding BW. In principle, E1 is the apical most electrode and E12 is the basal most electrode. The remaining electrodes E2 to E11 are preferably arranged in a relatively equally distributed manner therebetween. Given the individual shape of the cochlea of a patient and the specific insertion depth, which electrodes are arranged in the basal or helical winding cannot be defined in principle. The specific position of the electrodes E1 to E12 and the assignment of the electrodes E1 to E12 to the basal winding BW and apical winding AW is determined with the aid of the x-ray image or another suitable method.

Figure 5:
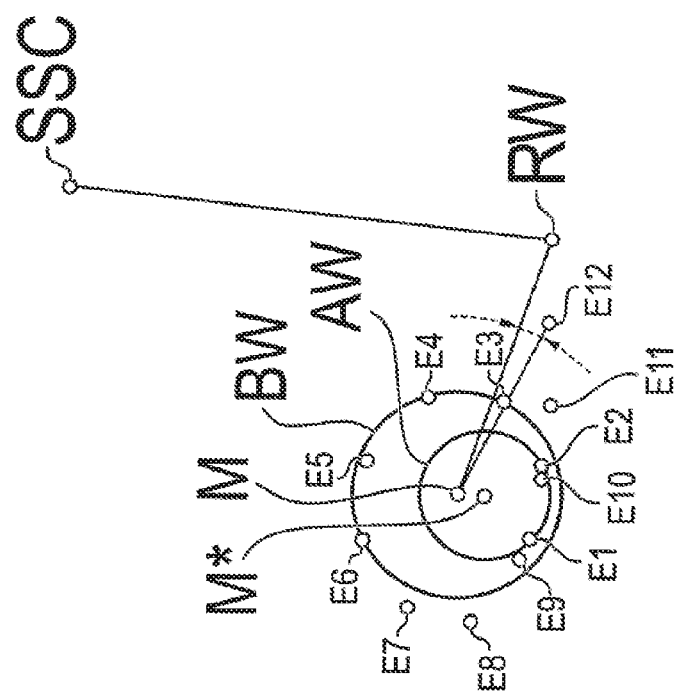
FIG. 5 a schematic drawing of the stimulation electrodes according to FIG. 4. including auxiliary lines for determining the insertion angle of the electrode E12.
Figure 4:
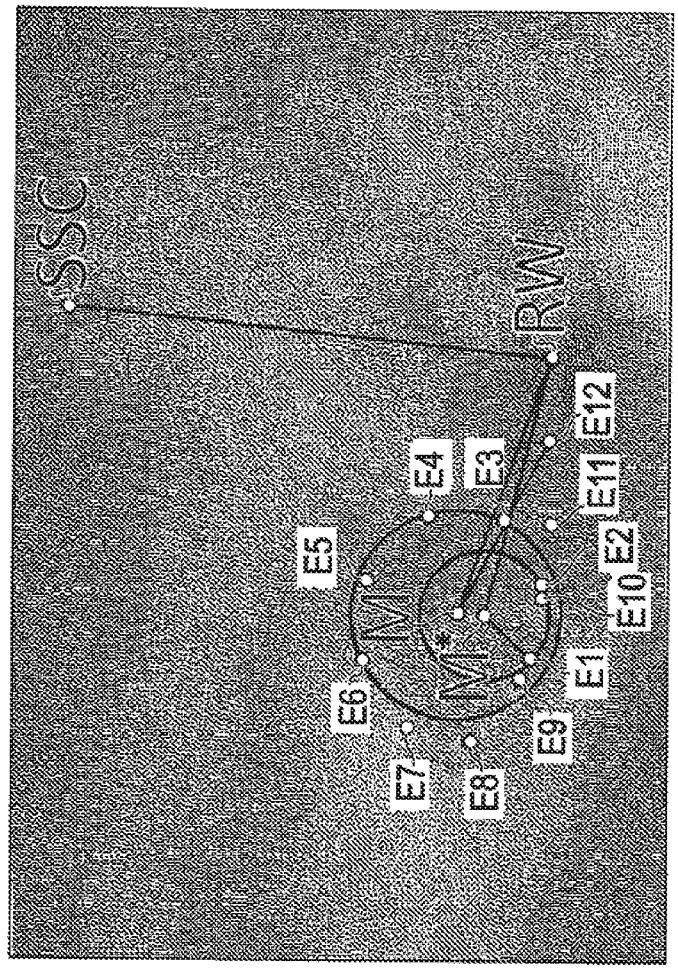
FIG. 4 the x-ray image according to FIG. 2 with additional auxiliary lines for determining the insertion angle of a second stimulation electrode E12.

The insertion angle of the electrode E12 determined according to the schematic representation according to FIG. 5 based on the x-ray image shown in FIG. 4 yields for the insertion angle 7.7 degrees.

The angle calculation is carried out on the basis of the above-mentioned Boex, C. et. al. In this case, the determined insertion angle is always oriented at the round window RW, i.e. both in the basal winding BW and in the apical winding AW. The angle has therefore been determined once in clockwise and once in the counterclockwise direction. If necessary, the determined insertion angle is subtracted from 360°. From Stakhovskaya, O.; Sridhar, D.; Bonham, B. H.; Leak, P. A. (2007): Frequency map for the human cochlear spiral ganglion: implications for cochlear implants. In: Journal of the Association for Research in Otolaryngology: JARO 8, p. 220-33. DOI: 10.1007/s10162-007-0076-9 a mathematical formula is known which indicates the relationship between the distance from the round window and the electrode insertion angle x for two different stimulation positions in the scala tympany:

$$y(x) = Ae^{-Bx} + C \qquad \text{(Equ. 1)}$$

where y(x) represents the percentage in length of the distance from the round window with respect to the total length of the range of the cochlea relevant for sound transmission in the value range between 0% and 100%.

The parameter sets are selected as follows:

$y_{SG}$: A=−99.3; B=0.004; C=105 for the spiral ganglia (SG)

$y_{GG}$: A=−110; B=0.002; C=115 for the cortical organ (OC)

Since the implanted electrode arrangement 12 is usually located in the scala tympani between the cortical organ and the spiral ganglia, for each electrode angle $x_i$ the mean value $y_m(x_i)$ from the parameter sets $y_{SG}$ and $y_{OC}$ is calculated as follows:

$$y_m(x_i) = \frac{y_{SG}(x_i) + y_{OC}(x_i)}{2} \qquad \text{(Equ. 2)}$$

Subsequently, with the aid of the method described from Greenwood, D. D. (1961): Critical Bandwidth and the Frequency Coordinates of the Basilar Membrane. In: J Acoust Soc Am 33 (10), pp. 1344-1356, the known equation for each electrode position $x_i$, a stimulation rate $F(x_i)$ adapted to this position is calculated in Hertz:

$$F(x_i) = D(10^{a(1-y_m(x_i))/100} - k) \qquad \text{(Equ. 3)}$$

Preferably the parameters are fixed to D=165.4; a=2.1; k=0.88.

The coupling of the triggering of an action potential of the auditory nerve to the phase of the electrical stimulation pulse (synchronization) is dependent on the stimulation rate, i.e. on the pulse rate. Due to the refractory time of the spiral ganglion cells of the auditory nerve, the synchronization already decreases above a stimulation frequency of 300 Hz. This behavior can also be observed in FIG. 6. The increase in the stimulation rate above 300 pps does not lead to a significant increase in the pitch perception. For this reason, a down-conversion of the stimulation rate at electrode positions $x_i$ with higher stimulation rates is useful. On the one hand, the energy demand required for the stimulation can be reduced in this way, on the other hand, the technical effort for generating the pulse patterns is reduced. In order to determine the down-conversion factor n, equation 4 is used. The stimulation rate $F(x_i)$ determined according to Equation 3 is divided by a divisor $f_u$ and the result is rounded up in order to determine an integer down-conversion factor n. According to Equation 5, an adjusted stimulation rate $F'(x_i)$ is below or equal to $f_u$. The parameter $f_u$ is adjusted in accordance with the individual refractory time of the auditory nerve and can, for example, be 1500 Hz.

$$n = \text{ceil}\left[\frac{F(x_i)}{f_u}\right] \qquad \text{(Equ. 4)}$$

where cell [ ] represents a rounding up function.

$$F'(x_i) = \left[\frac{F(x_i)}{n}\right] \qquad \text{(Equ. 5)}$$

Example $F(x_i)$ and $F'(x_i)$ for an implant with n=12 electrodes and $f_u$=1500 Hz:

| Electrode i | Insertion angle $x_i$ [degrees] | $F(x_i)$ [Hz] | $F'(x_i)$ [Hz] |
|---|---|---|---|
| E1 | 461.2 | 283.5 | 283.5 |
| E2 | 410.0 | 378.6 | 378.6 |
| E3 | 366.1 | 492.7 | 492.7 |
| E4 | 271.0 | 933.2 | 933.2 |
| E5 | 223.9 | 1341.7 | 1341.7 |
| E6 | 183.6 | 1890.7 | 945.4 |
| E7 | 176.7 | 2011.9 | 1005.9 |
| E8 | 153.7 | 2494.9 | 1247.5 |
| E9 | 115.8 | 3663.9 | 1221.3 |
| E10 | 59.2 | 7055.2 | 1411.0 |
| E11 | 25.7 | 10983.5 | 1372.9 |
| E12 | 7.7 | 14206.4 | 1420.6 |

The insertion angles of the electrodes E1 to E12 according to FIGS. 2 to 5 are specified in the above table. In addition, the individual pulse rate determined for the respective determined insertion angle is specified.

The method according the invention for determining the individual pulse rate for each electrode E1 to E6 has been tested with 11 single sided deaf persons using a cochlear implant. In this case, a test method described below was used. In this case, electrode E1 is the apical most electrode.

The according the invention parameterized stimulation rate for each of the electrodes E1 to E6 as a function of their actual position in the cochlea generates an individual pitch perception of a particular pitch in the test subjects. This pitch perception was determined in an experiment with the test method described in Baumann, U; Nobbe, A. (2006): The cochlear implant electrode-pitch function. In: Hear Res 213, pp 34-42. DOI: 10.1016/j.heares 2005.12.010. The task of the test subjects in this case was to assess the frequency (pitch) of an acoustic sinusoidal tone stimulation on the counter-ear relative to the perception with the aid of the cochlear implant in such a way that the acoustically stimulated sensation on the normal-auditory ear corresponds to the perceived pitch of the electrical stimulation on the ear supplied with the cochlear implant.

The stimulation was specified for each test person at six apical electrodes E1 to E6 with the aid of the method according to the invention. The pitch comparison was repeated six times for each electrode. The acoustic starting frequency at the normal-hearing ear was selected randomly in the range between 80 Hz and 8000 Hz, were in each case this was 3 times above and 3 times below the pulse rate of the stimulation pulses determined by the procedure according to the invention. The test person was asked to change the frequency of the acoustic stimulation by means of a rotary knob of a rotary pulser, in such a way that the pitch perception generated by the acoustic stimulation corresponds as precisely as possible to the pitch perception generated by the electrical stimulation. The test person signalizes the correspondence by pressing the rotary knob. No marking, which would have been made possible for the reproduction of a setting, was located on the rotary knob.

In order to control the individual electrodes E1 to E6, a special cochlear implant interface was used for carrying out the test explained above, namely the Research Interface Box II, (RIB II) of the Institute for Ion and Applied Physics, Innsbruck, Austria. This was used for the direct control of implants of the $SONATA_{T/100}$ device type and CONCERTO implants. Details about the Research Interface Box II are listed in Bahmer, A.; Peter, O.; Baumann, U. (2008): Recording of electrically evoked auditory brainstem responses (e-ABR) with an integrated stimulation generator in Matlab. In: journal of neuroscience methods 173, p. 306-14 DOI: 10.1016/j.jneumeth.2008.06.012.

The results of the tests carried out of the pitch control hearing experiment with the 11 test subjects are shown in FIGS. 7a to 7k in a total of 11 diagrams, wherein the test result of a test person is represented in a diagram in each case. Each data point in the diagrams represents the result of the pitch comparison of an electrode E1 to E6, where the pitch comparison was set by the determination of the median from six repetitions with randomized starting frequencies of the acoustic comparison sound. The electrical pulse rates determined according to the method according to the invention for the six apical most electrodes E1 to E6 of the cochlear implant are represented on the x-axis. Compared to previous examinations with other pulse rates, the results show substantially smaller intra-individual dispersions, which can be inferred from the formation of a salient pitch elevation impression by means of the electrodes controlled by the pulse rates determined according to the invention. All data can be approximated individually by means of a linear regression with a very large match. Thus, a correspondence with a degree of determination of $R^2>0.9$ has been achieved. The lines shown in the diagrams according to FIGS. 7a to 7k each show the linear regression of the test result for the respective test person.

Figure 8:
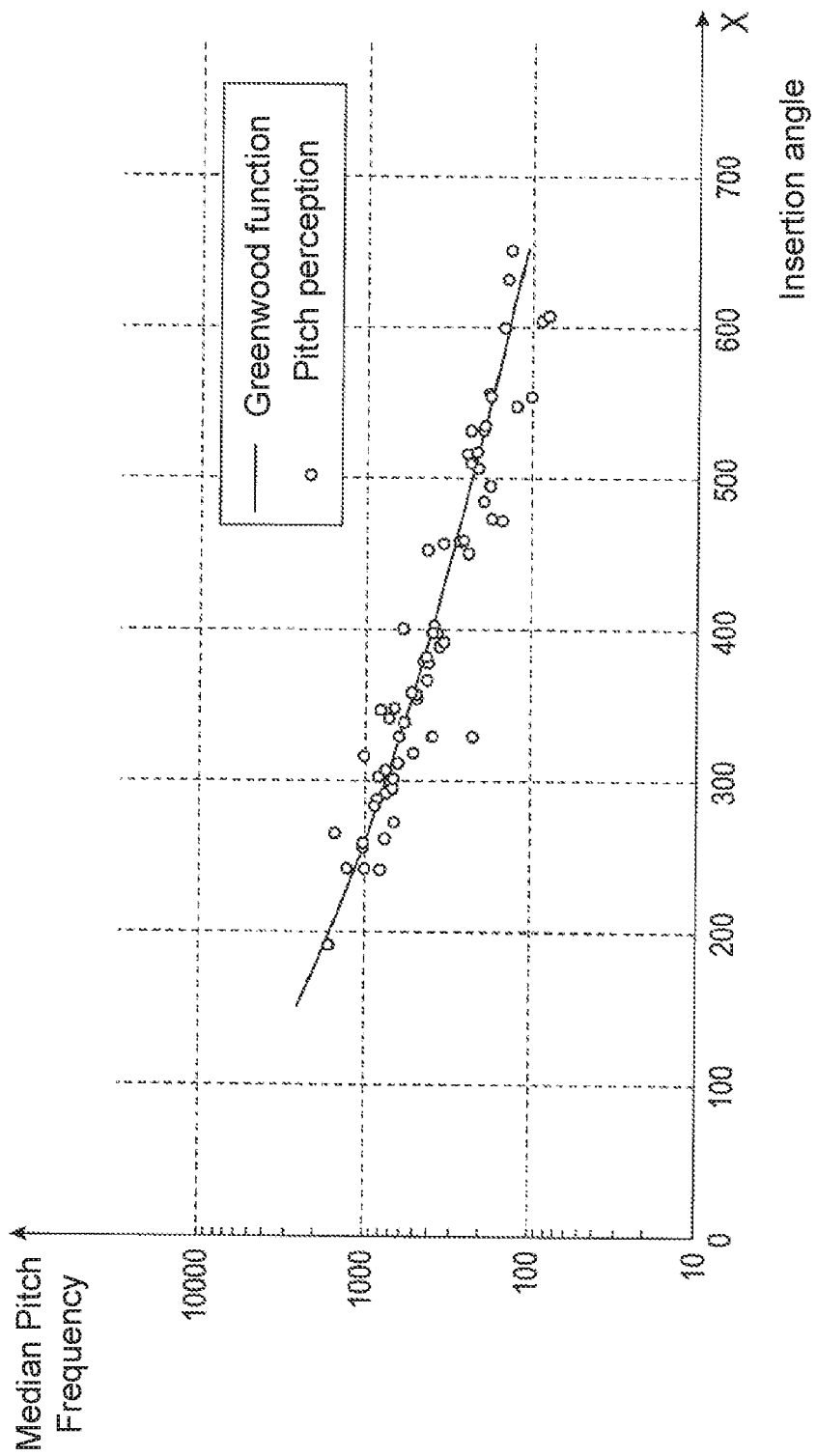
FIG. 8 a diagram with the determined mean pitch function compared to a reference function which is valid for normal hearing.

FIG. 8 shows the medians of the adjusted comparative pitch of all the test persons in dependency of the ascertained insertion angle in comparison to function by Greenwood, D. D. (1961): Critical bandwidth and the frequency coordination of the basilar membrane. In: J Acoust Soc Am 33 (10), pp 1344-1356. The results represented for a total of 66 electrodes show a high correspondence with a determination measure of $R^2=0.85$, which has previously not been achieved in any other procedure.

Figure 6:
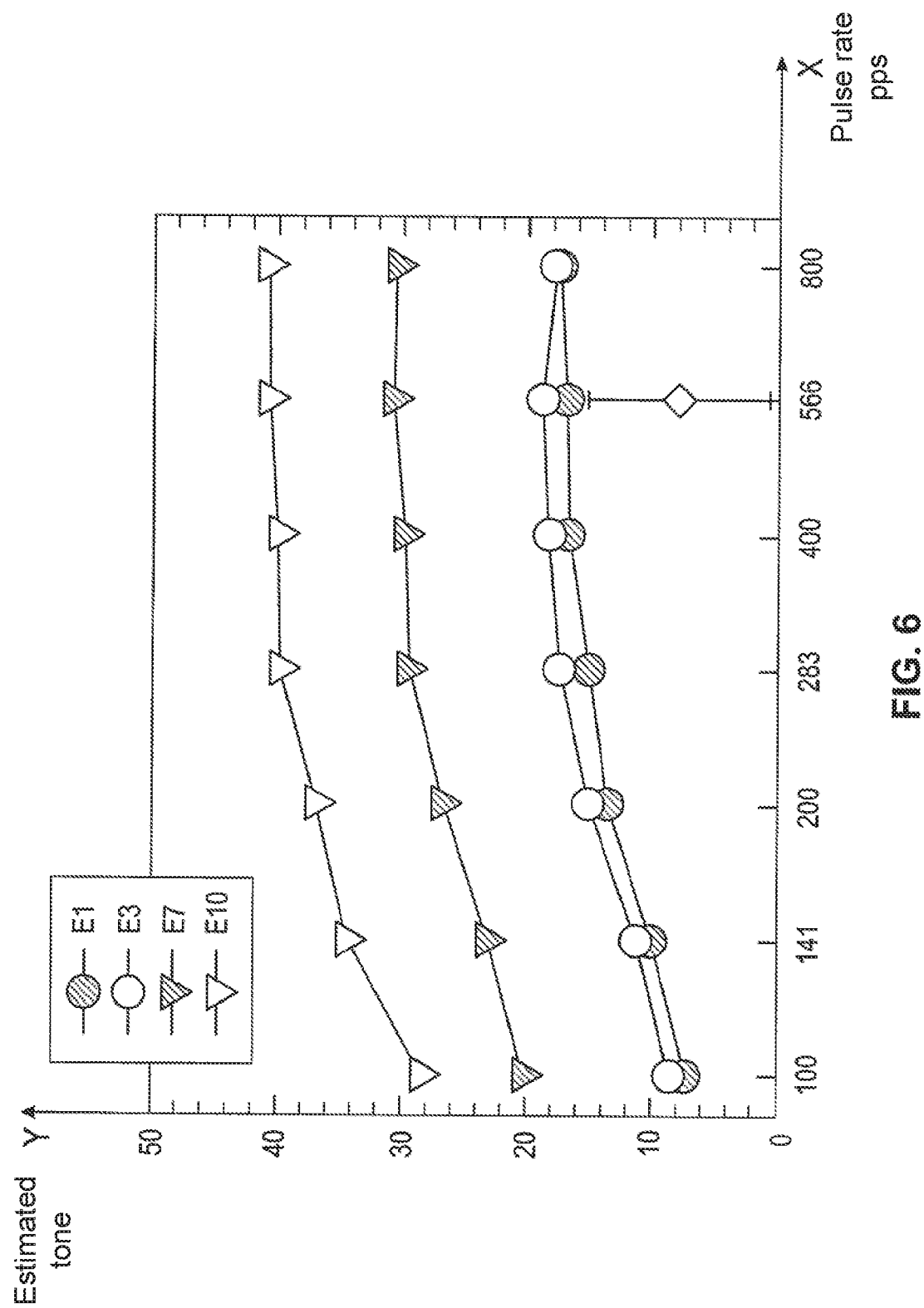
FIG. 6 a diagram with a representation of the subjective assessment of the pitch depending on the electrode position and the pulse rate as an arithmetic mean of experimental measurements in eight persons with cochlea implant, wherein E1 is the apical most electrode.
Figure 7A:
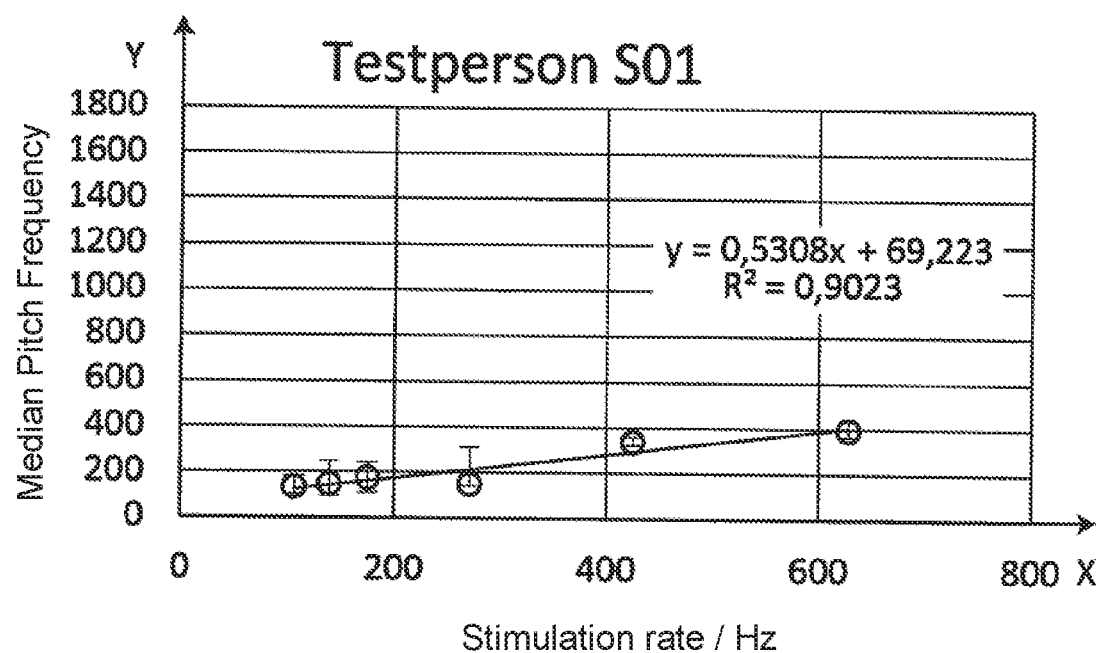
FIGS. 7a to 7k representations with in each case one test result of a pitch comparison experiment of a total of 11 single sided deaf test persons using a cochlear implant.
Figure 7B:
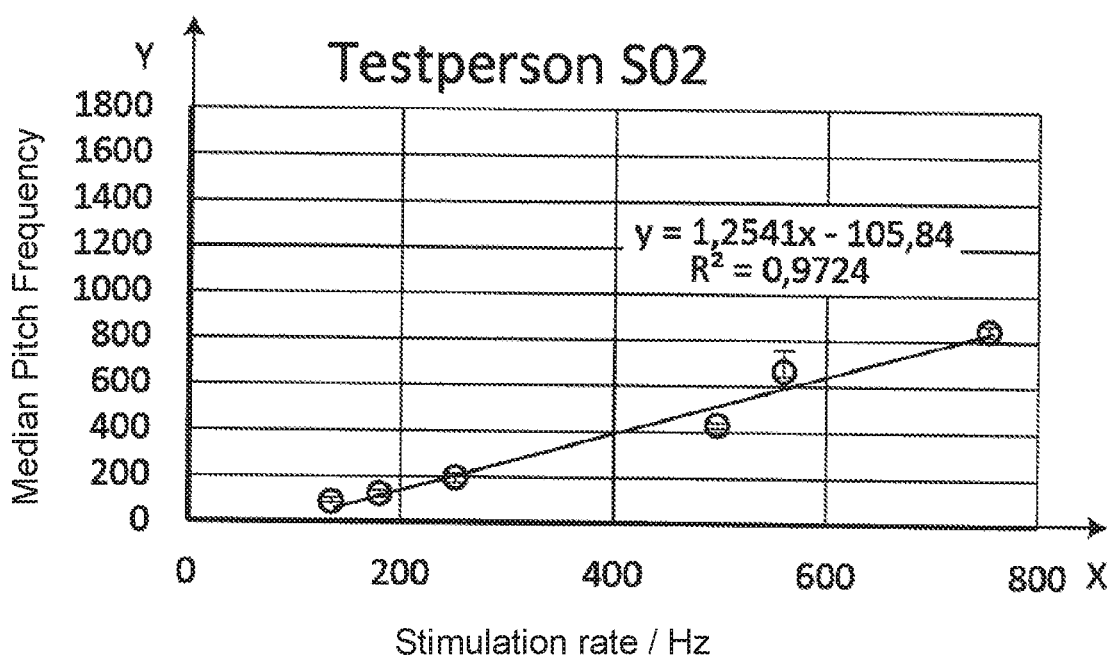
Figure 7C:
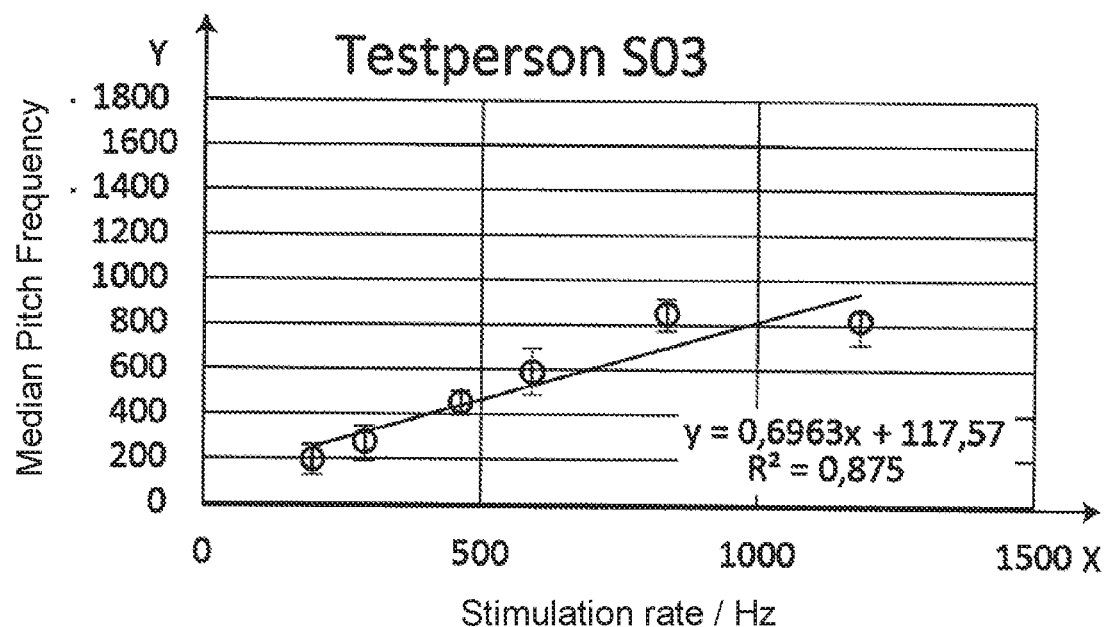
Figure 7D:
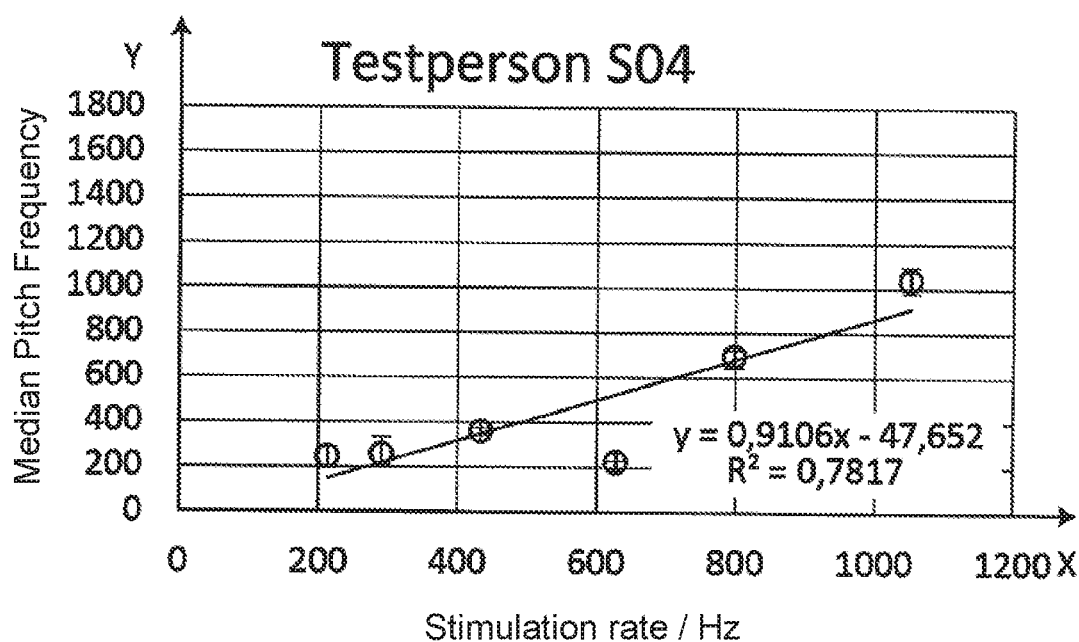
Figure 7E:
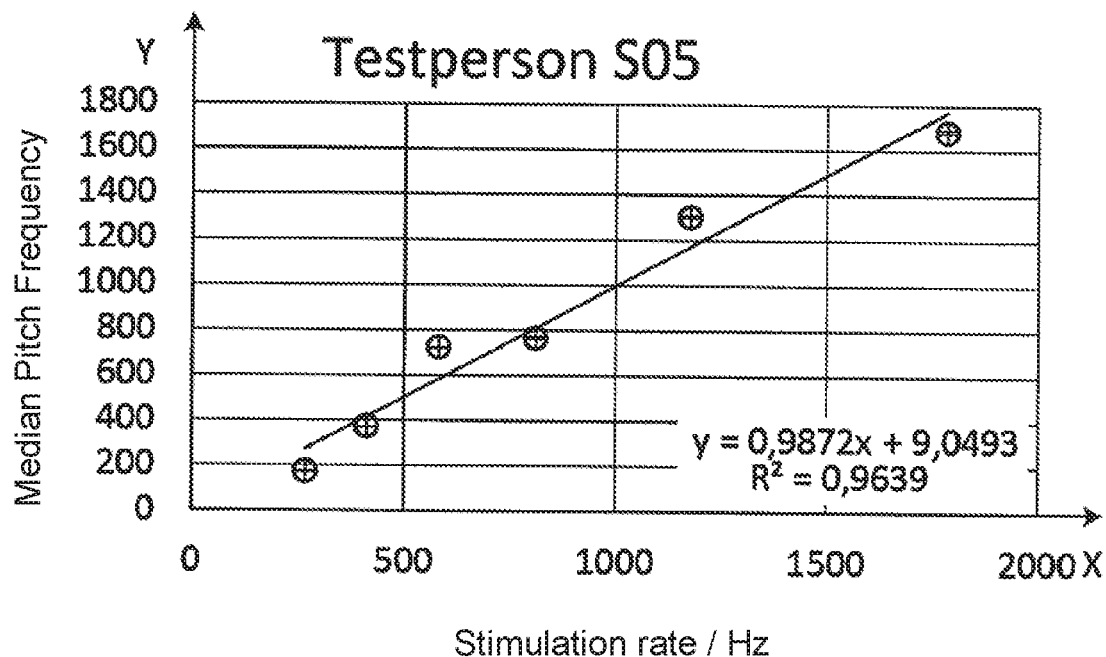
Figure 7F:
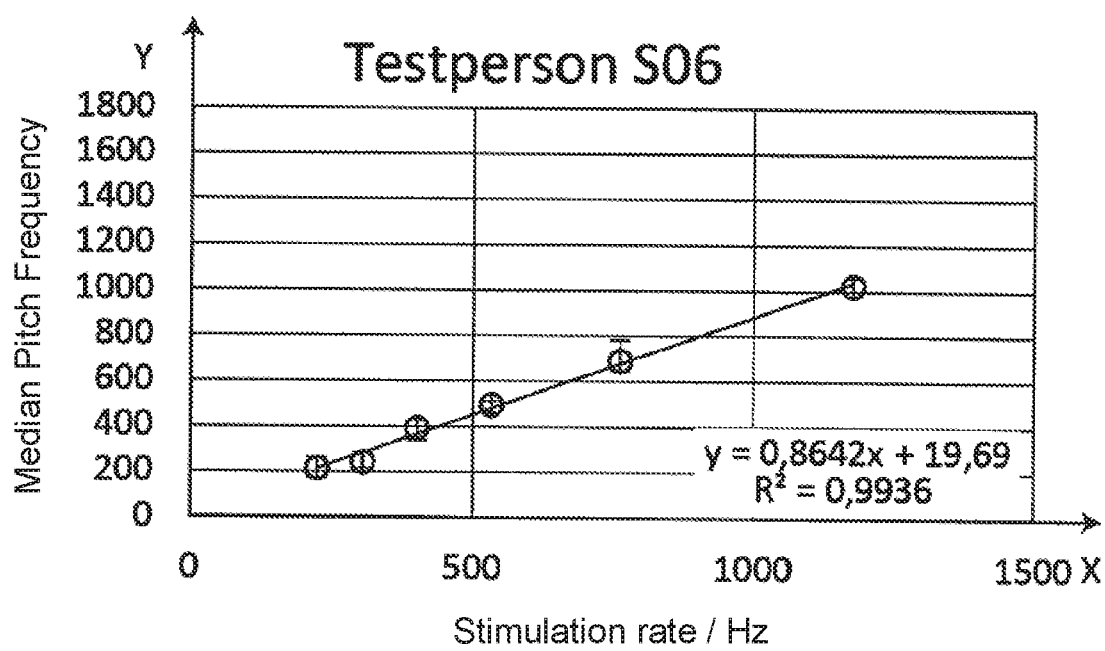
Figure 7G:
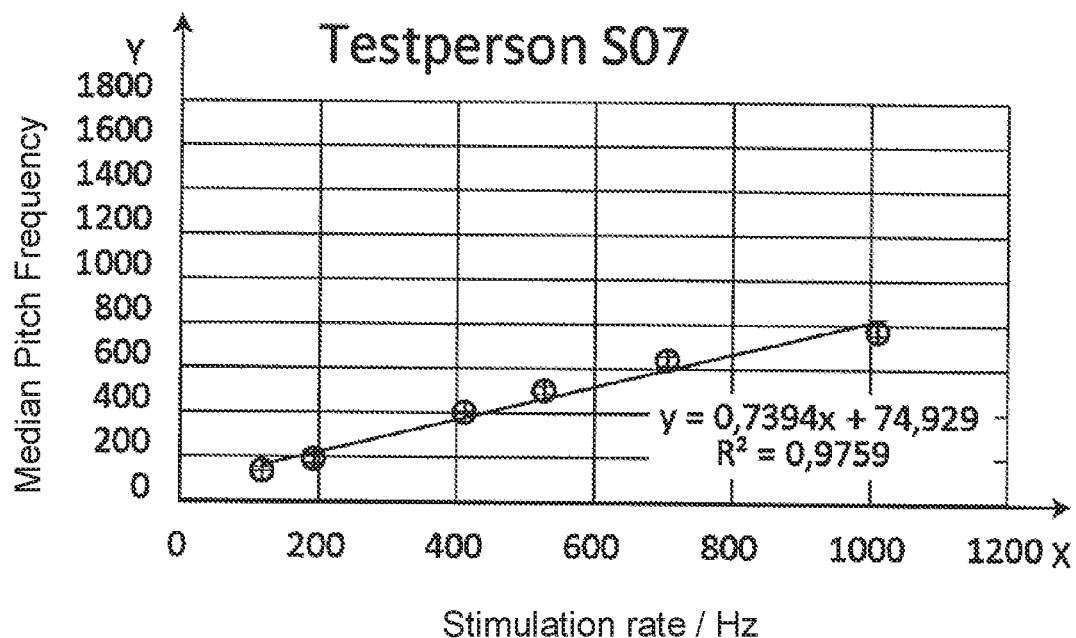
Figure 7H:
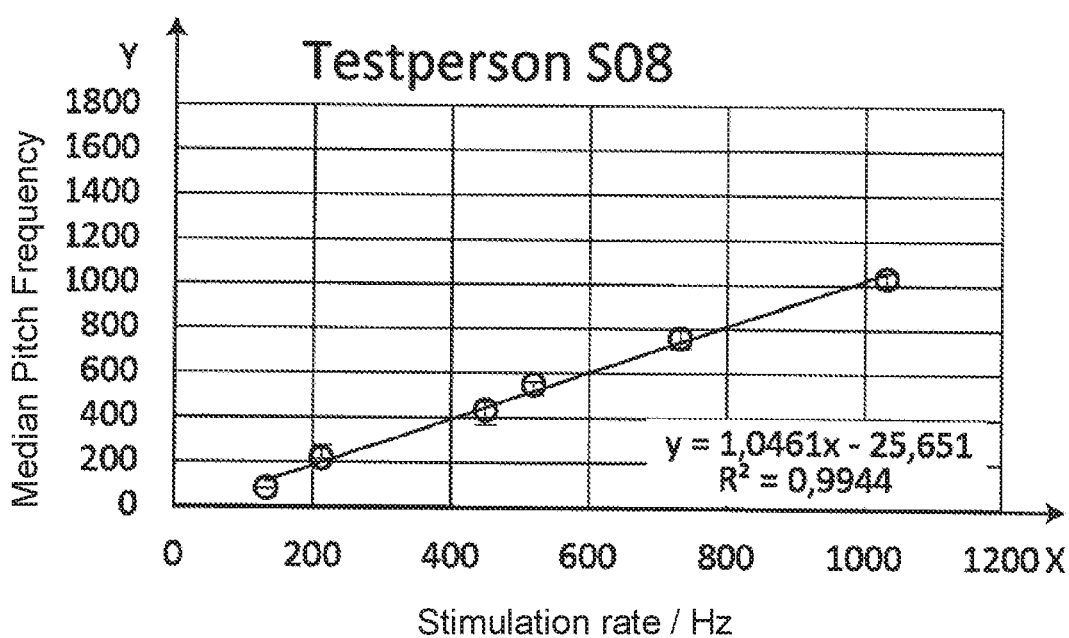
Figure 7I:
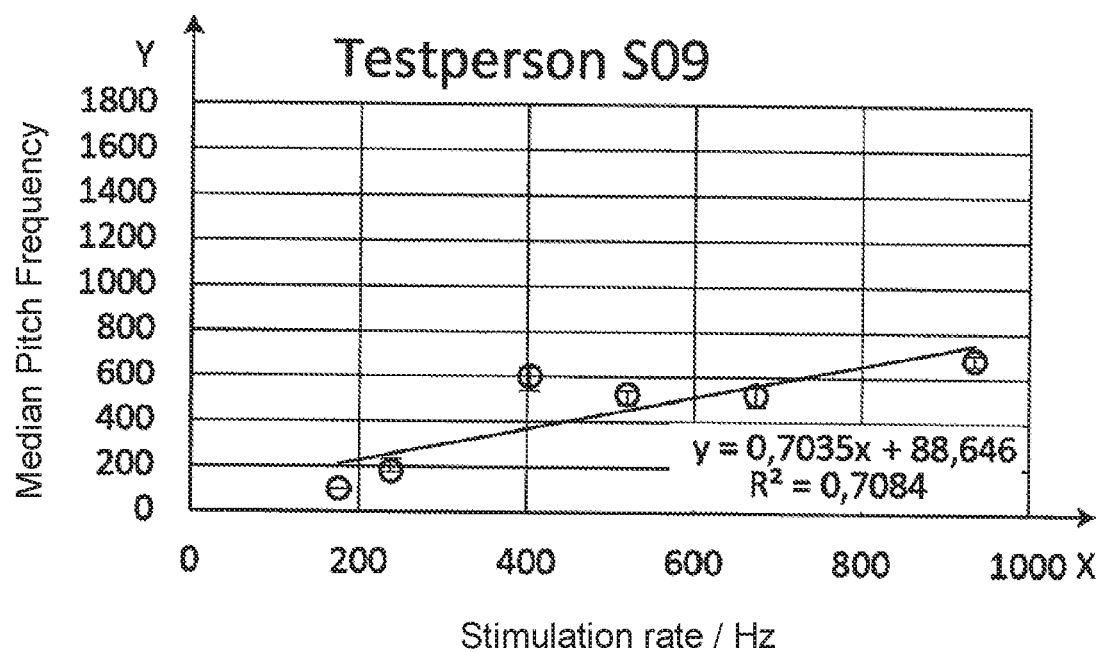
Figure 7J:
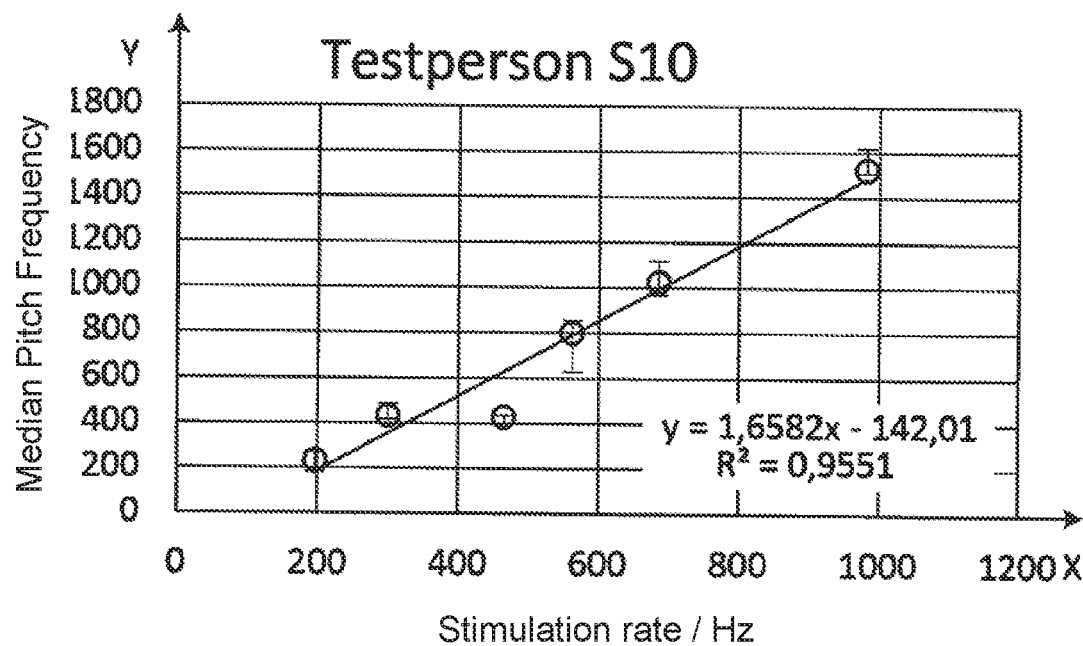
Figure 7K:
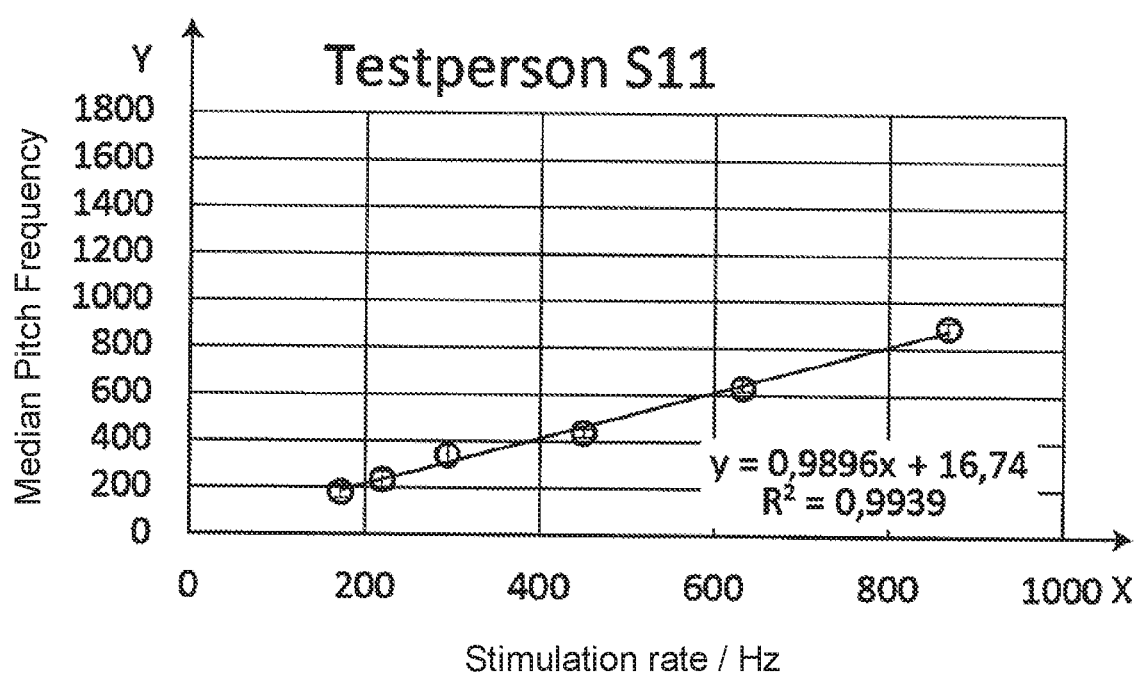

In contrast to the test results obtained for the electrodes E1 to E12 controlled by a pulse rate according the method of the invention is in FIG. 6 in Nobbe, A. (2004): Pitch perception and signal processing in electric hearing. HNO-Heilkunde. Ludwig-Maximlians Universitat of Munchen already published with the subjective assessment of the pitch of a total of eight test persons with a cochlear implant as a function of the electrode position. The electrode E1 is in this case apically arranged and the electrode E10 is basally arranged. The values stated for the electrodes E1, E3, E7 and E10 in the diagram are average values of the eight test persons. The applied pulse rate is on the x-axis, with which the respective electrode E1 to E10 has been triggered, and the estimated pitch is shown on the y-axis. This diagram shows that the pitch perception depends on the pulse rate and the position of the electrode E1 to E10 in the cochlea.

Figure 9:
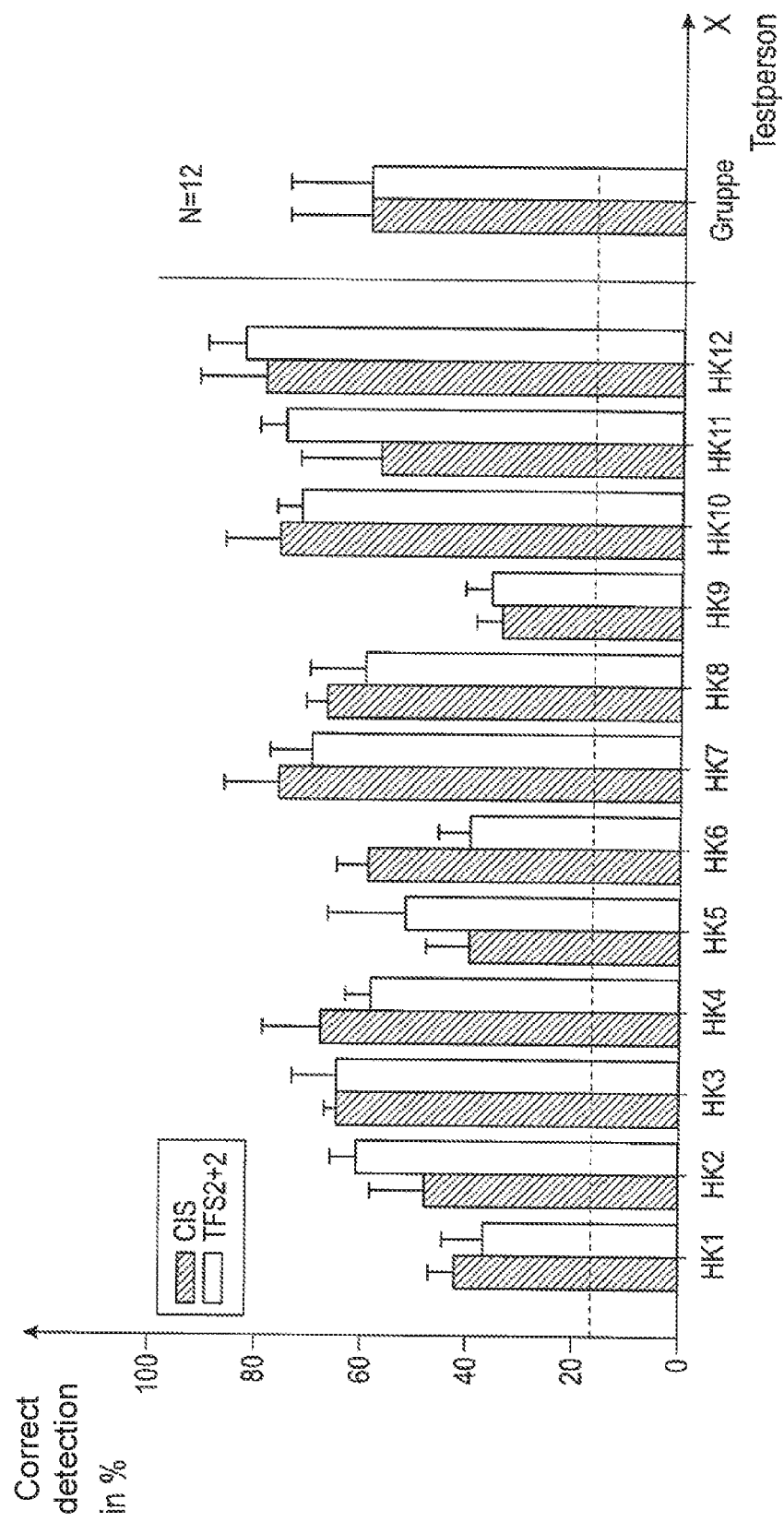
FIG. 9 a diagram showing the speech understanding of Cantonese phonetics as a comparison of conventional activation of a cochlear implant and control with a temporal fine structure.

FIG. 9 shows from the document, Schatzer R. (2010): Novel concepts for stimulation strategies in cochlear implants. Dissertation. University of Innsbruck, Innsbruck. Faculty of mathematics, computer science and physics. in an already published diagram, test results of tests carried out with 12 test persons for speech understanding of Cantonese sounds where the correct recognized speech of test persons with conventionally activated cochlea implants is compared with test persons having improved control known in the prior art of the cochlear implant. The diagram according to FIG. 9 shows a group evaluation in the right column, from which it can be seen, that the improved control of the electrodes in the prior art has no improvement compared to the conventional control of the electrodes. The improved control of the electrodes known in the prior art is based on a temporal fine structure, which is also referred to as TFS. In contrast to this, a considerably improved sound perception is achieved by the improvement of the pitch perception that is shown in FIG. 7 due to the control of the electrodes according to the invention, which also leads to an improvement in the identification of Cantonese tones information.

Figure 10:
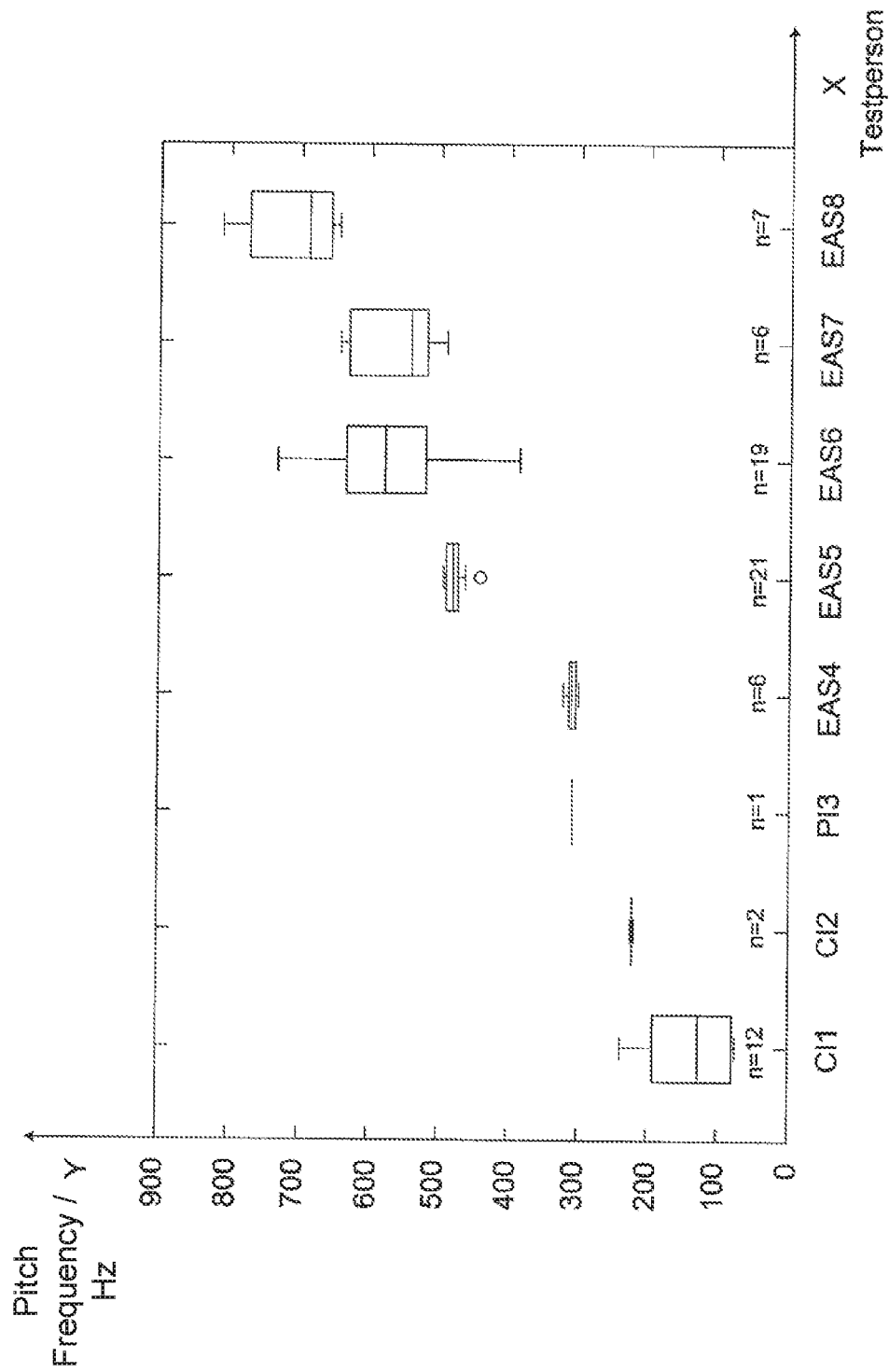
FIG. 10 shows a diagram with results of a pitch control parameter experiment without adaptation of the stimulation rate.

FIG. 10 shows a diagram with results of a pitch control experiment, as has also been explained for determining the sound level perception in conjunction with FIG. 7, wherein no adaptation of the stimulation rate to the position of the electrode in the cochlea is carried out. The subjects are marked in this diagram with CI1, CI2, PE3, EAS4, EAS5, EAS6, EAS7 and EAS8. In the case of the test person CI1, twelve calibration tests were carried out, for test person CI2 two calibration tests, for test person PE3 one calibration test, for test person EAS4 six calibration tests were carried out, for test person EAS5 21 calibration tests were carried out, for test person EAS6 19 calibration tests were carried out, for test person EAS7 six calibration tests were carried out and seven calibration tests were carried out for test person EAS8. The set frequencies shown on the y-axis fluctuate in particular in the test subjects EAS6 and EAS8 strongly, so that a relatively poor pitch perception independent of the for the electrodes and their position determined pulse rate is ascertained.

Known methods for controlling stimulation electrodes of a cochlear implant do not take into account the specific individual position of the individual stimulation electrodes E1 to E12 in the cochlea during the generation of the stimulation pulses. For the method according to the invention, the pulse rate for each individual stimulation electrode E1 to E12 is determined individually for the first time depending on the position data or position information obtained after the implantation of the stimulation electrodes E1 to E12. In contrast to the methods known from the prior art, the procedure according to the invention results in a tonotopy, which is close to the normal function of the perception of the pitch of a patient with a cochlear implant, as is shown in FIGS. 7a to 7k and FIG. 8.

Known control of the stimulation electrodes with a fixed stimulation rate generate only a very imprecise pitch perception for patients with a cochlear implant, as is explained in connection with FIG. 10. This variance of the pitch perception could be reduced by the procedure according to the invention in a significant manner for the test persons, as can be seen from FIGS. 7a to 7k. As a result, in the case of persons with a cochlear implant, the quality of the mapping of music signals and speech can be made more clearly and the enjoying of music or the understand of Cantonese sounds becomes the first time possible. In addition, speech understanding is also improved in in presence of noise. The transmission of prosodic information can also be improved compared to known control methods of stimulation electrodes.

REFERENCE NUMERAL LIST

10 Device
12 Stimulator
14 Receiving coil
16 Transmitting coil
18 Processor
20 Microphone
22 Battery
E1 to E12 Stimulation electrodes
M, M* Center point
BW Basal Winding
AW Apical Winding
SSC Superior curved path
RW Round window

What is claimed is:

1. A device for electrical stimulation, comprising:
a stimulator associated with a cochlear implant, the stimulator having a multi-channel electrode arrangement comprising a plurality of stimulation electrodes, and
a processor that determines the pulse rate and the pulse amplitude for each stimulation electrode and controls the electrode arrangement for delivery of stimulation pulses at the determined pulse rate and pulse amplitude, characterized in that the processor determines the pulse rate for each stimulation electrode depending on their position in the cochlea, wherein for each stimulation electrode an expected pitch perception is determined depending on their position in the cochlea, and wherein the pulse rate for a stimulation electrode corresponds to the frequency derived from the position in the cochlea, for the expected pitch perception, or is selected according the frequency corresponding to an integer multiple of the pulse rate that is derived from the expected pitch perception corresponding the position in the cochlea.

2. A device according to claim 1, wherein the processor controls the stimulation electrodes with the determined pulse rate.

3. A device according to claim 1, wherein the processor determines the pulse amplitude of the stimulation pulse delivered through the stimulation electrodes depending on the amplitude of the sound information to be stimulated.

4. A device according to claim 1, wherein the processor selects at least one stimulation electrode in dependence on the pitch of sound information to be stimulated and controls delivery of stimulation pulses for this stimulation electrode with the pulse rate determined for this stimulation electrode.

5. A device according to claim 1, wherein the processor determines the pulse rate for each stimulating electrode further dependent on the pitch of sound information to be stimulated.

6. A device according to claim 1, wherein the electrode arrangement comprises several monopolar stimulation electrodes.

7. A device according to claim 1, wherein the position of the stimulation electrode is determined by the angle of insertion.

8. A device according to claim 1, wherein starting from the position ascertained for each stimulation electrode, a basic tonotopy arrangement is determined.

9. A device according to claim 8, wherein the processor controls the pulse rate of each stimulation electrode independently, such that from the basic tonotopy arrangement a determined pitch perception is generated at the respective stimulation position.

10. A device according to claim 1, wherein the processor determines the pulse amplitude by a weighted parallel stimulation of neighboring stimulation electrodes.

11. A device according to claim 1, wherein the processor after setting the pulse rate and/or pulse amplitude tests whether a local increase of the electric field causes a too loud perception, wherein the processor reduces the number of pulses at a determined increase.

12. A method for controlling stimulation electrodes of a multi-channel electrode arrangement of a stimulator, wherein the pulse rate and the pulse amplitude for each stimulation electrode is determined, and wherein the electrode arrangement is controlled for delivery of the determined pulse rate and pulse amplitude, characterized in that: the position of each stimulation electrode in the cochlea is determined, and determining the pulse rate for each stimulation electrode depending on their position in the cochlea, wherein for each stimulation electrode an expected pitch perception is determined depending on their position in the cochlea, and wherein the pulse rate for a stimulation electrode corresponds to the frequency derived from the position in the cochlea, for the expected pitch perception, or is selected according the frequency corresponding to an integer multiple of the pulse rate that is derived from the expected pitch perception corresponding the position in the cochlea.

13. A computer program product comprising commands and data in encoded form that cause a data processing system after loading the program data, to determine the pulse rate for each stimulating electrode of a multichannel electrode arrangement associated with a cochlear implant, depending on their respective position within the cochlea, wherein for each stimulation electrode an expected pitch perception is determined depending on their position in the cochlea, and wherein the pulse rate for a stimulation electrode corresponds to the frequency derived from the position in the cochlea, for the expected pitch perception, or is selected according the frequency corresponding to an integer multiple of the pulse rate that is derived from the expected pitch perception corresponding the position in the cochlea.

14. A method determining the pulse rate for control of stimulation electrodes of a multi-channel electrode arrangement of a stimulator of a cochlear implant, comprising the steps of:
determining the position of an electrode of an implanted stimulator in the cochlea, and
determining the pulse rate for each stimulation electrode depending on their position in the cochlea, wherein for each stimulation electrode an expected pitch perception is determined depending on their position in the cochlea, and wherein the pulse rate for a stimulation electrode corresponds to the frequency derived from the position in the cochlea, for the expected pitch perception, or is selected according the frequency corresponding to an integer multiple of the pulse rate that is derived from the expected pitch perception corresponding the position in the cochlea.

15. The method of claim 14, wherein the position of a stimulation electrode is determined by using a radiographic method, in particular by planar X-ray, computed tomography, digital volume tomography or magnetic resonance tomography.

16. The method of claim 14, wherein the position of the stimulation electrode in the cochlea is determined by the angle of insertion.

17. The method according claim 14, wherein the expected pitch perception is calculated with the help of a mathematical function of the determined position of the stimulation electrode.

18. The method according to claim 14, wherein starting from the position ascertained for each stimulation electrode, a basic tonotopic arrangement is determined.

\* \* \* \* \*